(12) United States Patent
LaGreca, Sr.

(10) Patent No.: US 7,576,257 B2
(45) Date of Patent: Aug. 18, 2009

(54) RECLOSABLE WOUND DRESSING SYSTEM

(76) Inventor: Alfred J. LaGreca, Sr., 10 Paolo Rd., Hingham, MA (US) 02043

( * ) Notice: Subject to any disclaimer, the term of this patent is extended or adjusted under 35 U.S.C. 154(b) by 89 days.

(21) Appl. No.: 11/749,833

(22) Filed: May 17, 2007

(65) Prior Publication Data

US 2007/0282236 A1 Dec. 6, 2007

Related U.S. Application Data

(60) Provisional application No. 60/804,004, filed on Jun. 6, 2006.

(51) Int. Cl.
*A61F 13/00* (2006.01)
(52) U.S. Cl. .............. 602/58; 602/41; 602/42; 602/44; 602/54; 128/888; 128/889
(58) Field of Classification Search ............. 602/41–43, 602/48, 57, 44, 52, 54, 58; 128/888, 889; D24/189
See application file for complete search history.

(56) References Cited

U.S. PATENT DOCUMENTS

| 4,379,881 | A | * | 4/1983 | Peck ........................ 524/315 |
|---|---|---|---|---|
| 4,641,643 | A | * | 2/1987 | Greer ........................ 128/888 |
| 5,086,763 | A | | 2/1992 | Hathman |
| 5,702,356 | A | | 12/1997 | Hathman |
| 5,876,365 | A | | 3/1999 | Hart |
| D424,699 | S | | 5/2000 | Allen |
| D437,217 | S | | 2/2001 | Bloor et al. |
| 6,193,658 | B1 | | 2/2001 | Wendelken et al. |
| 6,940,000 | B1 | | 9/2005 | Davis |
| 6,966,320 | B1 | | 11/2005 | Baynes |
| 7,118,545 | B2 | | 10/2006 | Boyde |
| 2004/0249328 | A1 | | 12/2004 | Linnane et al. |
| 2005/0107732 | A1 | | 5/2005 | Boyde |

* cited by examiner

*Primary Examiner*—Kim M Lewis
(74) *Attorney, Agent, or Firm*—Brian M. Dingman; Mirick, O'Connell, DeMallie & Lougee, LLP

(57) ABSTRACT

A reclosable wound dressing system, comprising a base portion having a circumference and lower and upper sides, the lower side carrying an adhesive that adheres to the skin, the upper side defining a first part of a two-part mechanical fastener system, the base portion defining an open area within the circumference, and a covering portion having a lower side that defines the second part of the two-part mechanical fastener system, the covering portion overlying at least part of and engaging with the upper side of the base portion, the covering portion fully covering the open area of the base portion, to cover a wound located in the open area.

16 Claims, 2 Drawing Sheets

RECLOSABLE WOUND DRESSING SYSTEM

CROSS REFERENCE TO RELATED APPLICATION

This application claims priority of Provisional Patent Application Ser. No. 60/804,004 filed on Jun. 6, 2006, the disclosure of which is incorporated herein by reference.

FIELD OF THE INVENTION

The invention relates to a wound dressing.

BACKGROUND OF THE INVENTION

Wounds are often covered with a surgical pad such as gauze while they are healing. Gauze is typically held in place with surgical tape. In order to inspect the wound or change the dressing pad, the tape must be removed and excess adhesive residue cleansed from the skin. For wounds that require frequent care and take days to heal, this constant tape removal process often irritates and damages the skin, especially for diabetics, the elderly and those with sensitive skin. This causes pain, and can lead to infections or other serious side effects.

SUMMARY OF THE INVENTION

A purpose of the invention is to reduce the time required for nurses, doctors and patients to remove taped surgical pads from wounds for evaluation or for changing, as well as to reduce the negative factors related to the removing of the tape. The removal of tape, over the time required for wounds to heal, can cause scaring, infections and dermatitis. Further, the necessary repeated removal is very painful.

The invention has at least the following benefits:
Reduces hospital costs by reducing the time it takes a nurse to change a bandage.
Reduces waste disposal of adhesives.
Increases home care patient independence.
Reduces unnecessary bandage changes as wound and dressing can be evaluated without removal of bandage.
May reduce infection from bacteria.
Reduces pain, scarring and dermatitis caused by the daily changing of a bandage held to the skin with tape.
Allows bandage to be changed and wound to be evaluated or dressed as frequently as desired without irritation that is caused by tape removed from the skin.
Allows the type of dressing to be changed without having to remove the bandage.

This invention features a reclosable wound dressing system comprising a base portion having a circumference and lower and upper sides, the lower side carrying an adhesive that adheres to the skin, the upper side defining a first part of a two-part mechanical fastener system, the base portion defining an open area within the circumference, and a covering portion having a lower side that defines the second part of the two-part mechanical fastener system, the covering portion overlying at least part of and engaging with the upper side of the base portion, the covering portion fully covering the open area of the base portion, to cover a wound located in the open area.

The adhesive may comprise a butyl-based adhesive composition. The base portion may circumscribe the wound. The covering portion may overly essentially all of the base portion. The mechanical fastener system may comprise a two-part hook and loop fastener system, and the upper side of the base portion may define the hook part of the hook and loop fastener system. The reclosable wound dressing system may further comprise a dressing pad located in the open area of the base portion. The dressing pad may be in contact with the lower side of the covering portion. The dressing pad may be coupled to the lower side of the covering portion. The reclosable wound dressing system may further comprise a fastener member attached to the dressing pad that can be releasably coupled to the lower side of the covering portion. The fastening member may comprise one part of a two-part hook and loop fastener system, which is preferably the hook part.

The reclosable wound dressing system may further accommodate a drainage tube which is secured to the wound, lies upon a dressing pad which absorbs excess fluids, and extends out from the base and covering portions to allow drainage of a wound.

The cover portion and/or the base portion may define a pull-tab adapted to be gripped by a user to assist in separating the cover portion from the base portion. The cover portion may have an upper side comprising an outer substantially impervious skin, which may be opaque.

The reclosable wound dressing system may further comprise a removable protective member covering the adhesive on the lower side of the base portion.

Featured in a more specific embodiment is a reclosable wound dressing system comprising a base portion circumscribing the wound and having a circumference and lower and upper sides, the lower side carrying a butyl-based adhesive that adheres to the skin covered by a removable protective member, the upper side defining the hook part of a two-part hook and loop fastener system, the base portion defining an open area within the circumference, a covering portion having a lower side that defines the second part of the two-part mechanical fastener system, the covering portion overlying at least part of and engaging with the upper side of the base portion, the covering portion fully covering the open area of the base portion, to cover a wound located in the open area, and a dressing pad located in the open area of the base portion and in contact with the lower side of the covering portion.

BRIEF DESCRIPTION OF THE DRAWINGS

Other objects, features and advantages will occur to those skilled in the art from the following description of the preferred embodiments of the invention, and the accompanying drawings, in which.

DETAILED DESCRIPTION OF PREFERRED EMBODIMENTS OF THE INVENTION

Figure 1:
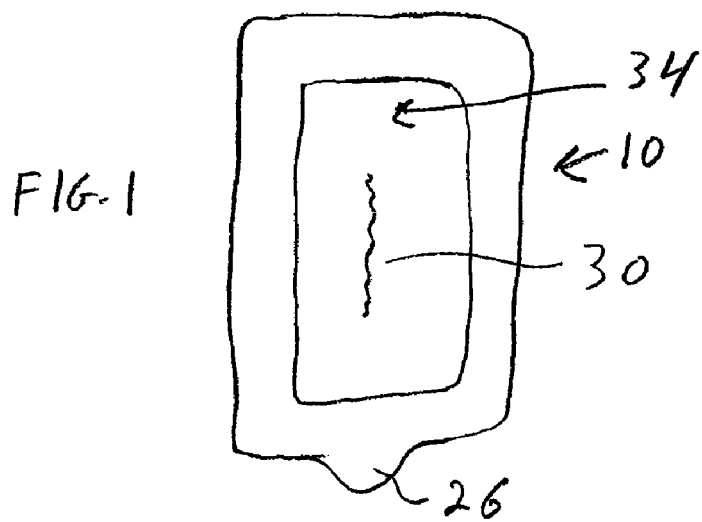
FIG. 1 is partial top view of the device of the invention in place surrounding a wound.
Figure 2:
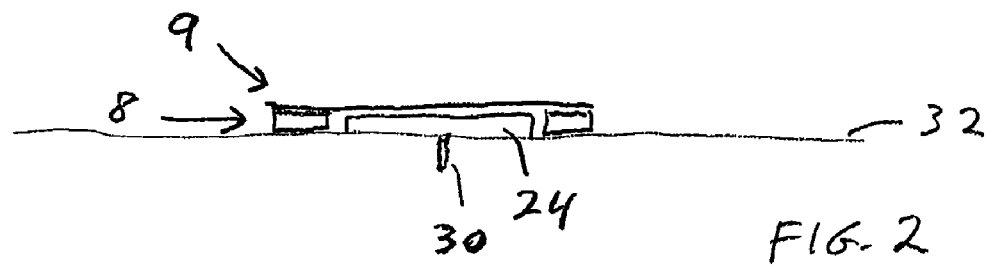
FIG. 2 is a cross-sectional view of the device of the invention in place on the skin.
Figure 3:
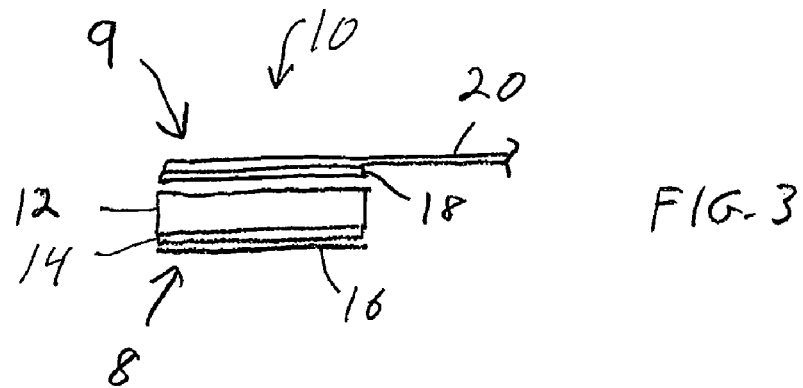
FIG. 3 is a partial, schematic, greatly enlarged cross-sectional view detailing the construction of one preferred embodiment.

This invention may be accomplished in a reclosable wound dressing system. A base portion carries on its lower side a long-term adhesive that adheres to the skin and can be left in place for about 5-7 days. The upper side defines a first part of a two-part mechanical fastener system such as a hook and loop fastener. The base portion defines an open area for the wound. A covering portion has a lower side that defines the second part of the two-part mechanical fastener system. The covering portion overlies and engages with the upper side of the base portion. The covering portion fully covers the open area of the base portion, to cover a wound located in the open area.

The inventive wound dressing system 10 has two basic components: a base member 8 that is adhered to skin surface 32, and a cover or top member 9. The bandage/dressing pad itself can be part of the invention, or can be held in place by the invention. The base member is an annulus or other shape that defines an open area. The base member is semi-permanently adhered to the skin, with the wound being treated located within the open area such that the base surrounds the wound, preferably without touching the wound. The top member either carries or holds in place, depending on the application, a gauze/dressing pad or other wound covering. The base member provides the function of a means to removably couple the top member to the skin. Removable coupling can be accomplished by making the base member and the top member of the complementary mating portions of a hook and loop fastener system such as that sold by the Velcro Company.

The adhesion of the base member to the skin is accomplished with an adhesive that is compatible with skin. The adhesive may be that used on NEXCARE absolute waterproof first aid tape by The 3M Company, or a hydrocolloid adhesive such as that disclosed in U.S. Pat. No. 4,952,618, for example. These adhesives may remain in contact to the skin for five to seven days under normal use, including movement and exposure to water, without loosening and without substantial negative impact to the skin. In the invention, tape is not used and the base member remains on the skin for multiple days. This obviates the need for frequent removal of tape from the skin that leads to so many problems in the current wound-care regiment.

The base can have a desired shape, such as circular or oval, for example. The preferred embodiment of the base member 8 comprises a strip of waterproof adhesive 14 approximately one half inch wide secured to the underside of an annulus 12 of the hook side of a VELCRO™ fastener system. The adhesive is used to secure the base to the person's skin, surrounding the wound. A preferred adhesive is 3M #9943 or #9944, or DUODERM™ by Convatec. The adhesive would normally be covered with a removable protective layer 16 as is commonly used to protect the sticky side of an adhesive tape, label or sticker. The base is preferably sterile, and can be made with anti-bacterial material.

Top member 9 is of the same size and perimeter shape as the base member, except that it is not annular. Accordingly, member 9 covers base member 8, and also spans opening 34 defined by the base member, to enclose the volume in which wound 30 is located, and also enclose dressing pad 24. Top member 9 can be constructed in two manners. In one manner, member 9 is a piece of fabric that defines loops that mechanically engage with the hooks of the base member. In a second manner of construction, the top member comprises an annulus 18 of the same size and shape as the base member, and defines the loop construction. In this case, top member 9 includes a plastic sheet 20 that is secured to the top portion 18 and spans the annular opening of portion 18. Top member 9 is sterile and can be made of anti-bacterial material. Member 9 may, through inclusion of loops, carry a dressing pad, in which case top member 9 is disposed of when the dressing pad is changed. Alternatively, sheet 20 may be used to enclose the volume in which dressing pad 24 is located, to hold the dressing pad in place covering the wound. This allows the dressing pad to be disposed of when changing the bandage, while retaining both the base member 8 and the top member 9 for reuse. In this case another dressing pad is inserted over the wound and sealed in place by pressing top member 9 to the base member 8. The exact configuration of the inventive system depends on the type of wound and specific dressing pad required. Sheet 20 can be opaque or translucent and/or hydrophobic, depending upon the material from which it is constructed. If it is translucent, the dressing pad can be inspected without separating the top member from the bottom member.

The top member can be a knit polyester fabric having loops that act as the loop portion of a hook and loop fastener system. The base member can be made from an extruded polypropylene. Both are available from Aplix, Inc. of Charlotte, N.C. (#N35 loop and #946 hook) or 3M (#7331 or #7333). In the case in which sheet 20 is used, it may be made from TEGADERM™ Film available from 3M, which is a breathable, waterproof layer which also provides a barrier to outside contaminants that can be adhered to the annulus 18 of loop-defining material.

Bottom member 8 and top member 9 may each have a projecting tab such as tab 26. The tabs provide an area that can be grasped by the user to hold down the base and provide for the easy release of the top member from the base member in order to access the wound.

The inventive system is a very low-profile wound covering that can stay in place for many days, thus decreasing the need to pull tape off of the skin in order to change a bandage. The result is less patient pain and suffering, and decreased costs associated with treating infections caused by repeated tape removal, which is prevalent in chronic-care situations in which a dressing may need to be changed multiple times per day, for a week or more. This also decreases medical costs by changing dressings only when necessary, decreased waste and decreased labor costs associated with removing tapes and their residue.

Application 1:

The sterilized base is removed from its sterile packaging and is attached to the skin approximately one inch away from and surrounding the incision, cut or wound to be protected. The top is removed from its sterile packaging. The top carrying the dressing is placed over the wound, aligning the top with the base. Light pressure to the top engages the hook and loop material to ensure a tight fit, and potentially a tight, waterproof or water resistant bandage.

Periodically (normal dressing change would be each day; chronic up to four times per day) the top is removed from the base by holding the base in place (tab 26) while pulling gradually on the tab (27) fixed to the top. The edges of the exposed area of skin are then dabbed with disinfectant and a new top carrying a dressing is applied to the base.

Application 2:

The base member and top member are removed from their sterile package. They can be arranged in a clamshell-type arrangement with the members attached together at one end. The top is separated from the bottom by use of the tab, and the appropriate dressing is applied. Periodically (normally dressing change would be each day; chronic up to four times per day) the top is peeled back from the base and a new dressing pad is applied. Both the base member and the top member are re-used during the entire course of wound treatment. If there is excessive drainage, the top may be replaced if necessary.

The invention speeds and eases wound care, and decreases incidence of tape removal-related infections. The invention thus can reduce the costs associated with wound care.

Figure 4:
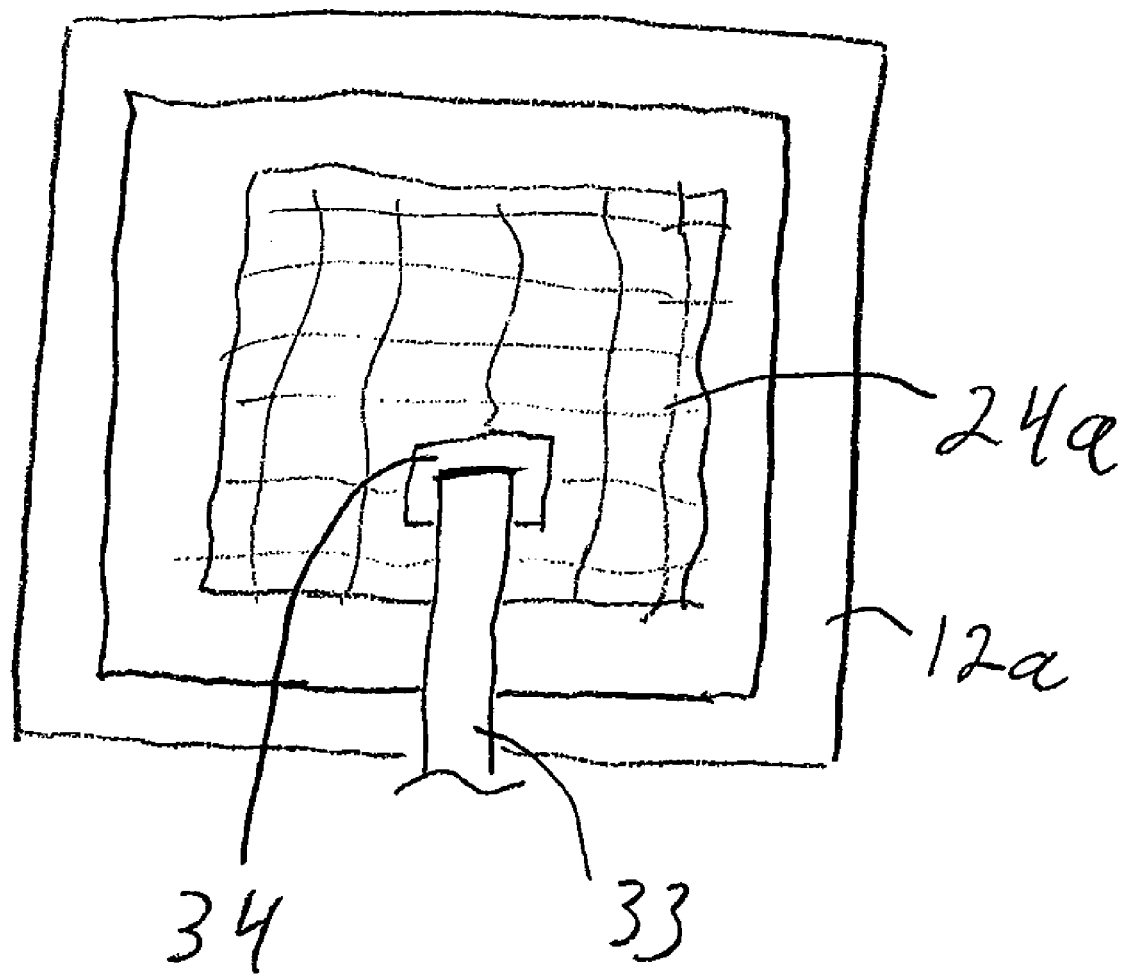
FIG. 4 is a partial top view of another embodiment that is adapted to also hold a wound drainage tube in place proximate the wound.

FIG. 4 shows the base member and dressing pad of another embodiment that is adapted to also hold a wound drainage tube in place attached within the body and extending from the wound. Base member 12*a* has a slit in one side so that it can be slipped under drainage tube 33. Dressing pad 24*a* has void area 34 to accommodate tube 33 where it emerges from the skin, and is placed around and under the drainage tube 33, to absorb excess fluid. A slot cut in drainage pad 24*a* allows the pad to be tucked under the tube. An opening or slit in the cover member (not shown) will allow for tube 33 to project through the inventive wound dressing system and be extended to a drainage vessel. The top member (not shown) is sufficiently flexible such that it can be attached to annulus 12 at all locations except where the top overlies tube 33 as it crosses over annulus 12*a*. The flexibility of the top member allows a tight enough fit over tube 33 such that it is held in place in the interior of the wound dressing system, and able to conduct fluid out away from the wound.

Although specific features of the invention are shown in some figures and not others, this is for convenience only, as some features may be combined with any or all of the other features in accordance with the invention.

Recitation of ranges of values herein are merely intended to serve as a shorthand method of referring individually to each separate value falling within the range, unless otherwise indicated herein, and each separate value is incorporated into the specification as if it were individually recited herein.

The use of any and all examples, or exemplary language (e.g., "such as") provided herein, is intended merely to better illustrate the invention and does not pose a limitation on the scope of the invention.

A variety of modifications to the embodiments described herein will be apparent to those skilled in the art from the disclosure provided herein. Thus, the invention may be embodied in other specific forms without departing from the spirit or essential attributes thereof.

What is claimed is:

1. A reclosable wound dressing system, comprising:
   a one-piece annular base member of the hook-part of a two-part hook and loop mechanical fastener system, the base member having lower and upper sides and a circumference, and defining an open area within the circumference, the hooks of the hook part located on the upper side of the base member;
   a strip of adhesive material that is adapted to adhere to skin, the adhesive material located directly on the lower side of the base member to adhere the base member to the skin;
   a one-piece top member annulus of knitted loop-part of the two-part hook and loop mechanical fastener system, the top member annulus overlying and directly engaging the upper side of the base member, so that the loops of the top member annulus directly couple with the hooks of the base member, the top member annulus having lower and upper sides and a circumference, and defining an open area within the circumference; and
   a waterproof breathable film directly coupled to the upper side of the top member annulus and fully covering the open area of the top member annulus, to cover a wound that is circumscribed by the base member.

2. The reclosable wound dressing system of claim 1 wherein the adhesive material comprises a butyl-based adhesive composition.

3. The reclosable wound dressing system of claim 1 further comprising a gauze pad located in the open area of the base member.

4. The reclosable wound dressing system of claim 3 wherein the gauze pad is in contact with the film.

5. The reclosable wound dressing system of claim 4 wherein the gauze pad is mechanically coupled to the film.

6. The reclosable wound dressing system of claim 5 in which the mechanical coupling is accomplished with a fastening member attached to the gauze pad that can be releasably coupled to the film.

7. The reclosable wound dressing system of claim 6 wherein the fastening member comprises one part of a two-part hook and loop fastener system.

8. The reclosable wound dressing system of claim 7 wherein the fastening member defines the hook part of the two-part hook and loop fastening system.

9. The reclosable wound dressing system of claim 1 further comprising a drainage tube that defines an inlet opening located in the open area, the drainage tube in contact with the lower side of the top member annulus and extending out from the base member and the top member annulus, to allow drainage of a wound encompassed by the base member.

10. The reclosable wound dressing system of claim 9 further comprising a gauze pad also located in the open area.

11. The reclosable wound dressing system of claim 10 wherein the gauze pad has a perimeter and defines an open area that communicates with the perimeter.

12. The reclosable wound dressing system of claim 11 wherein the inlet opening of the drainage tube is located in the open area of the gauze pad.

13. The reclosable wound dressing system of claim 11 wherein the top member annulus defines a pull tab adapted to be gripped by a user to assist in separating the top member annulus from the base member.

14. The reclosable wound dressing system of claim 1 wherein the film is opaque.

15. The reclosable wound dressing system of claim 1 further comprising a removable protective member covering the adhesive material on the lower side of the base member.

16. A reclosable wound dressing system, comprising:
   a one-piece annular base member of the hook-part of a two-part hook and loop mechanical fastener system, the base member having lower and upper sides and a circumference, and defining an open area within the circumference, the hooks of the hook part located on the upper side of the base member;
   a strip of butyl-based adhesive material that is adapted to adhere to skin, the adhesive material located directly on the lower side of the base member to adhere the base member to the skin;
   a removable protective member covering the adhesive;
   a one-piece top member annulus of knitted loop-part of the two-part hook and loop mechanical fastener system, the top member annulus overlying and directly engaging the upper side of the base member, so that the loops of the top member annulus directly couple with the hooks of the base member, the top member annulus having lower and upper sides and a circumference, and defining an open area within the circumference;
   a waterproof breathable film directly coupled to the upper side of the top member annulus and fully covering the open area of the top member annulus, to cover a wound that is circumscribed by the base member; and
   a gauze pad located in the open area of the base member in contact with the skin.

* * * * *

UNITED STATES PATENT AND TRADEMARK OFFICE
CERTIFICATE OF CORRECTION

| | | |
|---|---|---|
| PATENT NO. | : 7,576,257 B2 | Page 1 of 1 |
| APPLICATION NO. | : 11/749833 | |
| DATED | : August 18, 2009 | |
| INVENTOR(S) | : Alfred J. LaGreca, Sr. | |

It is certified that error appears in the above-identified patent and that said Letters Patent is hereby corrected as shown below:

Column 6, line 29, should be corrected as follows:

The reclosable wound dressing system of claim "11" --1--

Signed and Sealed this

Twentieth Day of October, 2009

David J. Kappos
*Director of the United States Patent and Trademark Office*